(12) United States Patent
Okoba

(10) Patent No.: US 9,086,397 B2
(45) Date of Patent: Jul. 21, 2015

(54) AUTOMATIC SAMPLER

(71) Applicant: SHIMADZU CORPORATION, Kyoto-shi, Kyoto (JP)

(72) Inventor: Tsutomu Okoba, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 442 days.

(21) Appl. No.: 13/732,572

(22) Filed: Jan. 2, 2013

(65) Prior Publication Data

US 2014/0182396 A1    Jul. 3, 2014

(51) Int. Cl.
*G01N 1/14* (2006.01)
*G01N 35/10* (2006.01)
*G01N 35/00* (2006.01)

(52) U.S. Cl.
CPC .. *G01N 35/1016* (2013.01); *G01N 2035/00217* (2013.01)

(58) Field of Classification Search
None
See application file for complete search history.

(56) References Cited

FOREIGN PATENT DOCUMENTS

| JP | 3023466 U | 1/1996 |
|---|---|---|
| JP | 08-145975 A | 6/1996 |
| JP | 2005-265805 A | 9/2005 |
| JP | 2006-133139 A | 5/2006 |
| JP | 2007-040932 A | 2/2007 |

OTHER PUBLICATIONS

Japanese Office Action dated Jun. 11, 2013, issued in corresponding Japanese Patent application No. 2010-156851, w/English translation.

*Primary Examiner* — Robert R Raevis
(74) *Attorney, Agent, or Firm* — Westerman, Hattori, Daniels & Adrian, LLP

(57) ABSTRACT

A weight sensor for measuring the weight of a sample container is fixed to a sample container placing portion. The amount of sample contained in the sample container placed in the sample container placing portion is determined based on a measurement value by the weight sensor. A change in amount of sample contained in the sample container is determined before and after sample suction by a sample suction mechanism. The amount of sample actually suctioned from the sample container is determined based on the change.

3 Claims, 5 Drawing Sheets

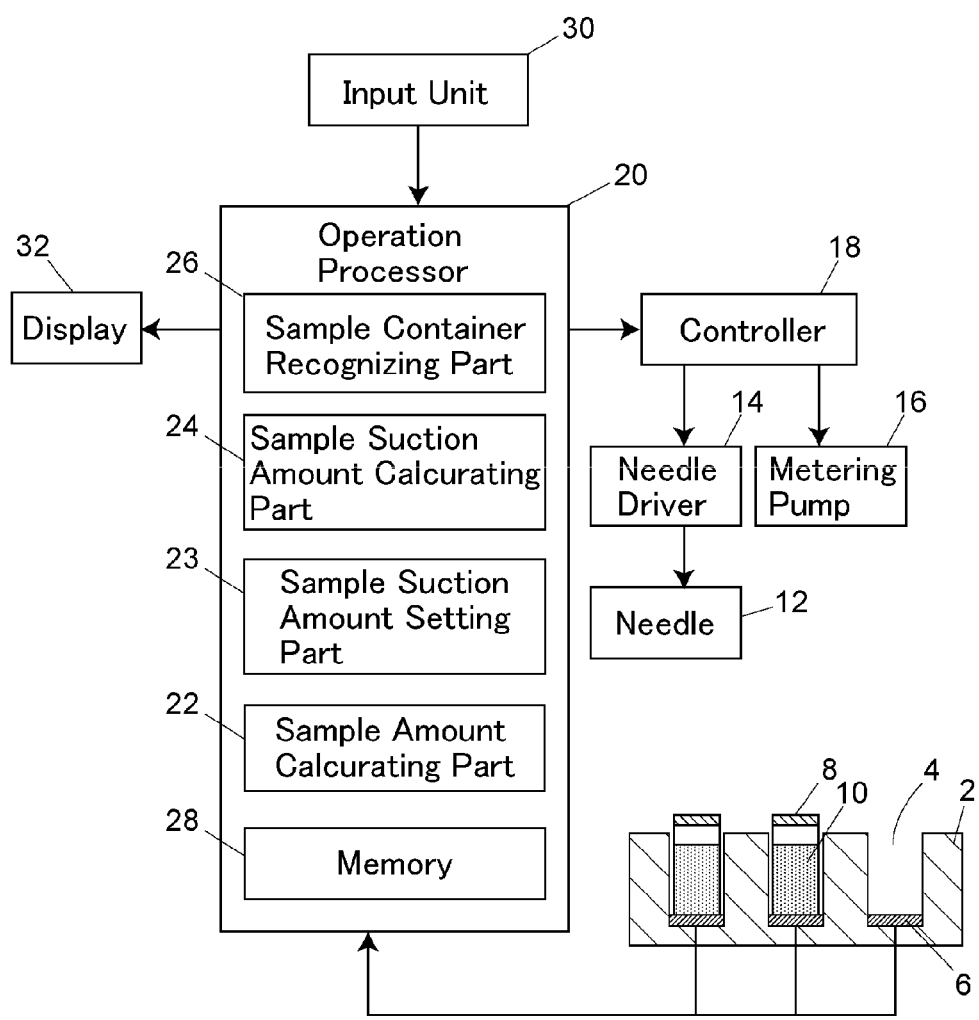

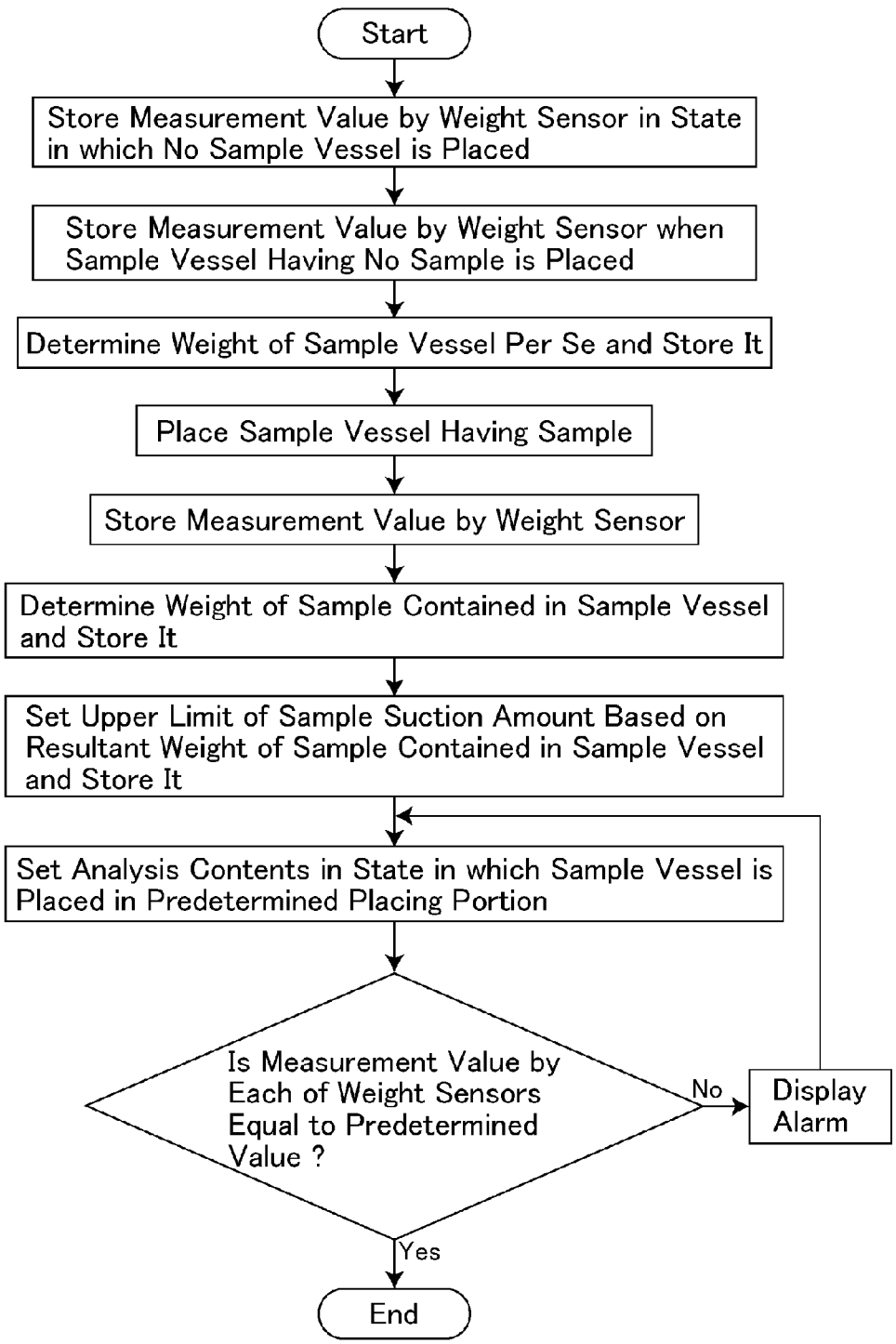

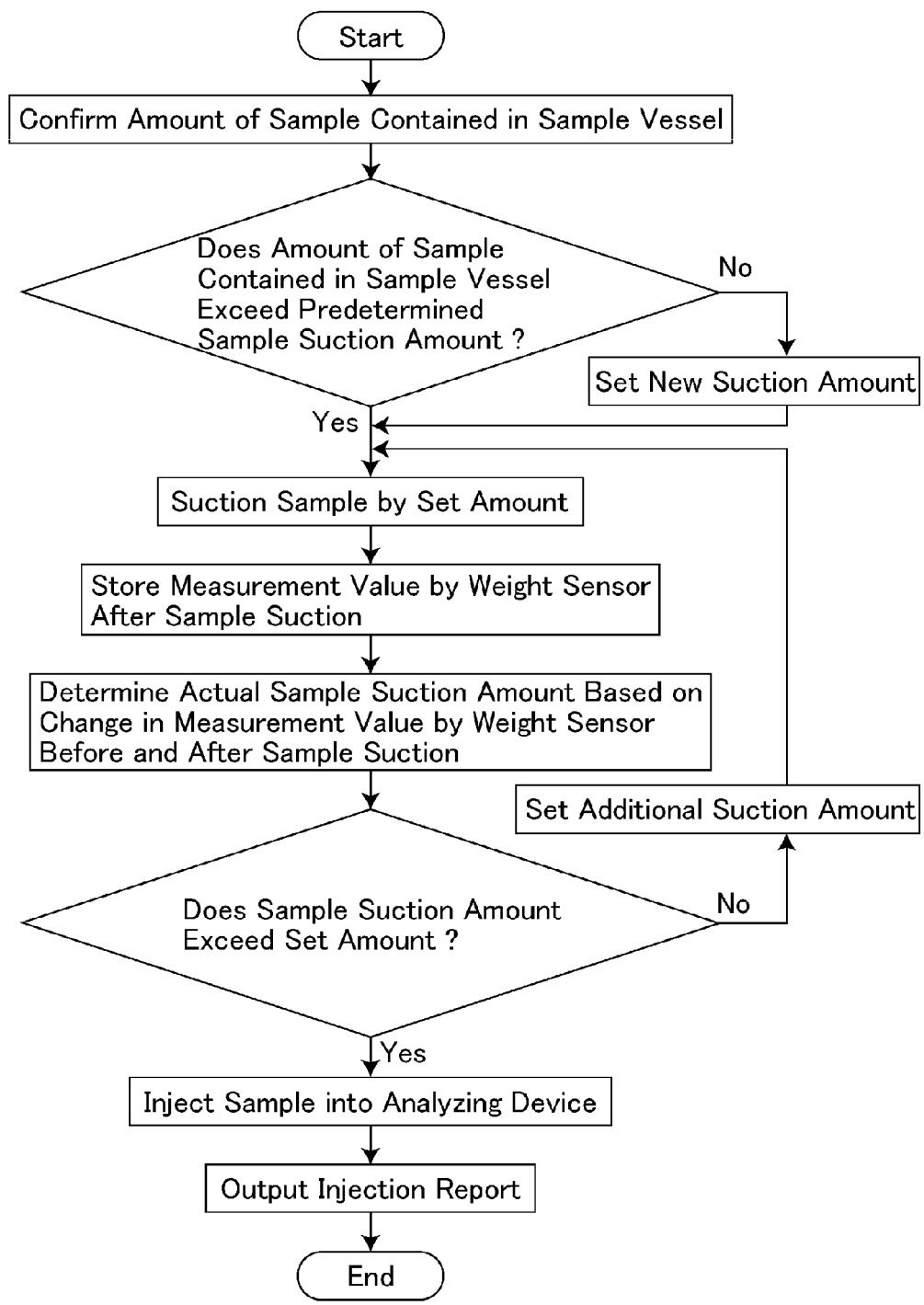

US 9,086,397 B2

AUTOMATIC SAMPLER

BACKGROUND OF THE INVENTION

1. Field of the Invention

The present invention relates to an automatic sample injecting apparatus (hereinafter referred to as an "automatic sampler") for suctioning a sample from a sample container containing the sample so as to inject the suctioned sample to an analyzing device such as a liquid chromatograph.

2. Description of the Related Art

An automatic sampler is generally provided with a needle for suctioning and ejecting a sample, a mechanism for moving the needle, a metering pump, and a valve for switching connection between a plurality of passages (see, for example, Unexamined Patent Application Publication No. 2005-265805).

There are two systems for an automatic sampler: a total amount injection system and a loop injection system. In an automatic sampler of a total amount injection system, a sample loop is connected between a needle and a metering pump via a valve, to then be filled with a sample suctioned in a larger amount than the volume of the sample loop, followed by switching the valve in such a manner as to connect the sample loop onto a passage of an analyzing device, so that the sample is injected to the analyzing device by the amount equivalent to the volume of the sample loop. In other words, in the automatic sampler of the total amount injection system, the volume of the sample loop per se is basically equivalent to the amount of the sample to be injected to the analyzing device, and therefore, the reproducibility of the amount of sample to be injected to the analyzing device is excellent. However, with this system, the sample spilling from the sample loop is discharged to a drain, and therefore, the sample is largely consumed.

In contrast, in an automatic sampler of the loop injection system, a sample loop is positioned on a base end side of a needle. A predetermined amount of sample suctioned by a metering pump is made to stay in the sample loop, and then, the sample is injected to an analyzing device. That is to say, in the automatic sampler of the loop injection system, the amount of sample suctioned by the metering pump is equivalent to the amount of sample to be injected to the analyzing device. Therefore, a suction error made by the metering pump signifies an error of the injection amount as it is, thereby affecting the reproducibility of the amount of sample to be injected to the analyzing device.

In the case where deficient suction occurs in the metering pump or the amount of sample in the sample container is insufficient in the automatic sampler, the amount of sample to be injected to the analyzing device is smaller than the predetermined amount, thereby possibly affecting an analysis result. This problem is more conspicuous in the loop injection system. Only the amount of sample less than or equal to the volume of the sample loop can be possibly suctioned due to deficient suction by the metering pump also in the total amount injection system, thereby raising a problem.

In order to confirm whether or not the sample is normally suctioned from the sample container, an analyzer needs to take out a rack including the sample containers before and after an analysis, measure the weight of the sample container by using a scale, and determine a decrease in weight of the sample contained inside of the sample container. In the case where the determined amount of suctioned sample is different from a predetermined value, a calibration coefficient is determined by using the determined amount of suctioned sample and the predetermined amount of suctioned sample. The resultant calibration coefficient needed to be multiplied by a signal strength obtained by the analysis for the purpose of correction. Here, the calibration coefficient is a coefficient obtained by dividing a predetermined suction amount by an actual suction amount. For example, in the case where the actual suction amount is only 90% of the predetermined suction amount, the calibration coefficient becomes 1.11 obtained by dividing 1 by 0.9.

As described above, in order to verify whether or not the sample is normally suctioned from the sample container, the analyzer needed to measure the decrease in amount of sample contained inside of the sample container after the analysis so as to confirm the decrease. However, this verification requires the manual work of the analyzer, thereby raising the problems of an increase in time and labor, and further, occurrence of artificial errors.

There has been known an analyzing device in which a weight sensor is disposed in a scale having a solution bottle mounted thereon, a sensor signal cable is connected to an input terminal, and then, a sensor signal is input into the input terminal when the weight of the solution bottle becomes a predetermined value or lower, thus stopping a system or issuing an alarm, so as to prevent an idle operation of the system (see Unexamined Patent Application Publication No. 8-145975).

SUMMARY OF THE INVENTION

In view of the above, an object of the present invention is to readily confirm the amount of sample actually suctioned from a sample container.

An automatic sampler according to the present invention includes: a sample container placing portion for placing a sample container containing a sample therein; a sample suction mechanism for suctioning the sample from the sample container placed in the sample container placing portion; a weight sensor fixed to the sample container placing portion, for measuring the weight of the sample container placed in the sample container placing portion; a sample suction amount setting part for setting the amount of sample to be suctioned from the sample container by the sample suction mechanism; a controller for controlling the sample suction mechanism in such a manner that the sample suction mechanism suctions the sample from the sample container by the amount set in the sample suction amount setting part; a sample amount calculating part for determining the amount of sample in the sample container placed in the sample container placing portion based on a measurement value detected by the weight sensor; and a sample suction amount calculating part for determining the amount of sample actually suctioned from the sample container based on a change in amount of sample contained in the sample container, determined by the sample amount calculating part before and after the sample suction by the sample suction mechanism.

It is preferable that the sample suction amount setting part includes an additional suction amount setting part for setting an amount equal to a shortage as an additional suction amount in the case where the sample suction amount determined by the sample suction amount calculating part is short by the predetermined amount or more with respect to the amount set in the sample suction amount setting part. In this case, the controller is configured to control the sample suction mechanism in such a manner that the sample suction mechanism further suctions the sample from the sample container by the additional suction amount set in the additional suction amount setting part. Hence, in the case of occurrence of deficient suction, an apparatus automatically suctions the sample by the shortage, so that the sample can be injected into an analyzing device in the amount approximate to the amount set by an analyzer. Thus, it is possible to enhance the injection accuracy of the sample with respect to the analyzing device, and it is unnecessary for the analyzer to calibrate an analysis result based on the actual sample suction amount.

It is preferable that the sample suction amount setting part includes a suction amount change setting part for setting the amount less than or equal to the amount of sample contained in the sample container again as a suction amount change when the amount of sample contained in the sample container determined by the sample amount calculating part before the sample suction by the sample suction mechanism is less than the predetermined suction amount. In view of this, the sample cannot be suctioned in an amount more than that of sample contained in the sample container, so that air cannot be trapped in a pump or a passage on the analyzing device.

Moreover, it is preferable that the automatic sampler further comprises: a container weight holding part for holding a weight of a sample container in the state in which no sample is contained; and a sample container recognizing part for issuing an alarm on a display in the case where a measurement value by the weight sensor is less than the weight of the sample container held by the container weight holding part. The case where the measurement value by the weight sensor is smaller than the weight of the sample container held by the container weight holding part signifies the case where no sample container is placed in the sample container placing portion. In this case, when an alarm is displayed, the analyzer can readily recognize that he or she forgets placing the sample container, so as to prevent a sample suction operation from being performed in the state in which no sample container is placed. If the sample suction operation is performed in the state in which no sample container is placed, the sample suction mechanism suctions air. Therefore, the air may be trapped on the pump or the passage of the analyzing device, resulting in trouble.

According to the present invention, the weight sensor is fixed to the sample container placing portion, and further, the sample suction amount calculating part is provided for calculating the amount of sample actually suctioned from the sample container based on a change in measurement value by the weight sensor before and after the sample suction. Consequently, the amount of sample actually suctioned from the sample container can be automatically calculated. Thus, no manual measurement of the sample suction amount is needed, thereby facilitating verification whether or not the sample suction mechanism normally suctions the sample.

BRIEF DESCRIPTION OF THE DRAWINGS

FIG. 1A is a block diagram schematically illustrating a preferred embodiment of an automatic sampler;

FIG. 2 is a flowchart explanatory of a preparing operation in the preferred embodiment of the automatic sampler;

FIG. 3 a flowchart explanatory of an analyzing operation in the preferred embodiment of the automatic sampler;

TABLE 1 is a table illustrating one example of an injection report to be output to a display in the preferred embodiment of the automatic sampler.

DETAILED DESCRIPTION OF THE INVENTION

Figure 1B:
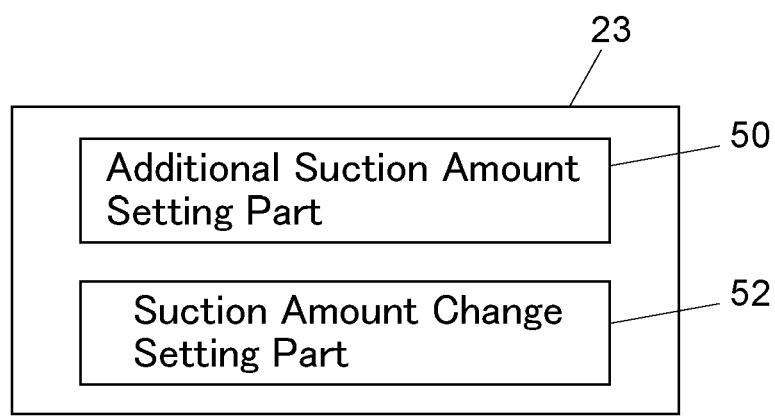
FIG. 1B is a block diagram illustrating a preferred embodiment of a sample suction amount setting part in the automatic sampler shown in FIG. 1A.

One example of an automatic sampler will be described with reference to FIG. 1.

A rack 2 is provided for containing sample containers 8 therein, and further, has a plurality of sample container placing portions 4, in each of which the sample container 8 is placed. A weight sensor 6 is placed at the bottom of each of the sample container placing portions 4. The weight sensor 6 is, for example, a piezoelectric transducer (i.e., piezo element) or a pressure sensor element that can measure the weight of the placed sample container 8.

A sample suctioning mechanism for suctioning a sample from the sample container 8 comprises a needle 12, a needle driver 14, and a metering pump 16. The needle driver 14 is adapted to drive the needle 12 inward on a horizontal plane and in a vertical direction. The needle 12 is moved to the sample container 8 containing therein a sample 10 to be suctioned by the needle driver 14, and then, its tip is inserted into the sample contained inside of the sample container 8. The metering pump 16 is designed to suction and eject the sample via the needle 12.

The needle driver 14 and the metering pump 16 are controlled by a controller 18. The controller 18 is adapted to perform a control in response to a signal output from an operation processor 20. The operation processor 20 includes a sample amount calculating part 22, a sample suction amount setting part 23, a sample suction amount calculating part 24, a sample container recognizing part 26, and a memory 28.

The memory 28 stores therein a measurement value by each of the weight sensors 6 in the state in which no sample container 8 is placed in the sample container placing portion 4, a measurement value by each of the weight sensors 6 in the state in which the sample container 8 containing no sample is placed in the sample container placing portion 4, information such as a specific gravity of a sample contained in the sample container 8, and the like. The memory 28 performs the container weight holding part by storing the measurement value by each of the weight sensors 6 in the state in which the sample container 8 containing no sample is placed in the sample container placing portion 4.

The sample container recognizing part 26 confirms whether or not the measurement value by each of the weight sensors 6 becomes a value previously set by an analyzer, and then, recognizes whether or not a proper sample container 8 is placed or whether or not the sample container 8 is placed. In the case where the sample container recognizing part 26 cannot recognize that the proper sample container is placed in the sample container placing portion 4, an alarm is issued to the analyzer by displaying the matter on a display 32 or the like.

The sample amount calculating part 22 reads the measurement value by the weight sensor 6 in the state in which the sample container 8 containing a sample 10 therein is placed, and then, subtracts, from the measurement value, the measurement value by the weight sensor 6 (that is stored in the memory 28) in the state in which the sample container 8 containing no sample is placed, thereby calculating the amount of sample contained inside of the sample container 8. The calculated sample amount is stored in the memory 28. Although the sample amount may be calculated based on the weight, the sample amount may be calculated based on a volume if the weight is divided by the specific gravity of the sample.

In the case where a value obtained by inputting the amount of sample to be suctioned from each of the sample containers 8 via an input unit 30 by the analyzer is proper, the sample suction amount setting part 23 sets it as a sample suction amount. The case where the input value is proper signifies the case where the input value is lower than or equal to the amount of sample contained in the sample container 8 that is previously measured and stored in the memory 28. In contrast, in the case where the input value exceeds the amount of sample contained in the sample container 8 that is previously measured and stored in the memory 28, the amount of sample contained in the sample container 8 is set as a sample suction amount. Here, in the case where the amount of sample actually contained in the sample container 8 is a predetermined value or lower (e.g., 30% or less of the set suction amount), the sample suction to the sample container 8 may be stopped. It is because an analysis result cannot be accurately produced with a high sensitivity even if the sample is analyzed in an extremely smaller amount than the amount of sample to be inherently injected into the analyzer. Moreover, also when no sample container 4 is placed in the sample container placing portion 4, the sample suction is stopped.

The controller 18 reads a signal from the operation processor 20 according to the value set in the sample suction amount setting part 23, and then, controls the needle driver 14 and the metering pump 16 in such a manner as to suction the sample from each of the sample containers 10 according to the set suction amount. Here, in the case where the set suction amount is different from the sample suction amount input by the analyzer, the calibration coefficient is determined by dividing the input sample suction amount by the set suction amount, thereby correcting the analysis result by the analyzing device. The calibration coefficient may be determined by the analyzing device that has obtained information on the sample suction amount from the operation processor 20 or may be determined by the operation processor 20.

The sample suction amount calculating part 24 calculates the amount of sample actually suctioned by the needle 12 based on a change in amount detected by the weight sensor 6 before and after the sample is suctioned by the needle 12. The timing when the sample suction amount is calculated is, for example, immediately after the sample is suctioned and before the needle 12 is pulled out of the sample container 8. When the actual sample suction amount calculated herein is smaller than that set in the sample suction amount setting part 23, the sample suction amount setting part 23 sets a value obtained by subtracting the actual sample suction amount from the set value as an additional suction amount to an additional suction amount setting part 50. When the additional suction amount is set, the controller 18 controls the metering pump 16 in such a manner as to further suction the sample by the additional suction amount. Incidentally, the additional suction amount is set in the case where a difference between the actual suction amount calculated by the sample suction amount calculating part 24 and the set value is large. Whether or not the difference between the calculated amount and the set value is large depends on whether or not the difference is, for example, 10% or more of the set value.

In a preferred embodiment, the sample suction amount setting part 23 may be provided with the additional suction amount setting part 50 and/or a suction amount change setting part 52, as illustrated in FIG. 1B.

The controller 18 and the operation processor 20 may be implemented by a dedicated computer for this automatic sampler or a general-purpose personal computer. The sample amount calculating part 22, the sample suction amount setting part 23, the sample suction amount calculating part 24 and the sample container recognizing part 26 are functions performed by the computer.

In the following, operation in the preferred embodiment will be explained.

[Preparation]

Figure 4:
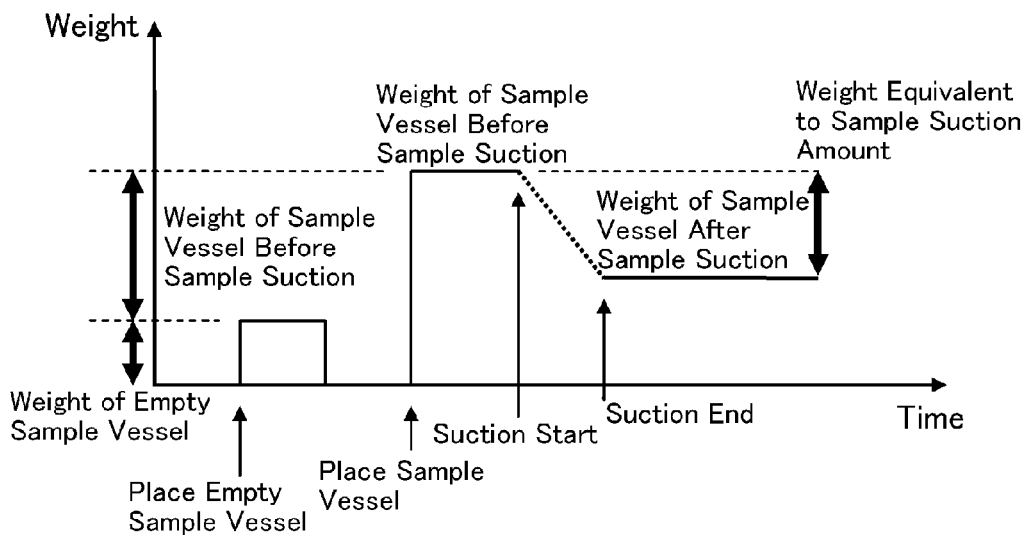
FIG. 4 is a graph illustrating changes in measurement values by a weight sensor according to operation in the preferred embodiment of the automatic sampler.

Preparation will be described with reference to FIGS. 1, 2, and 4.

First of all, the memory 28 stores therein a measurement value by each of the weight sensors 6 in the state in which no sample container is placed in the sample container placing portion 4 in the rack 2. Thereafter, the sample container 8 having no sample is placed in each of the sample container placing portions 4. The memory 28 stores therein the measurement value by each of the weight sensors 6 at this time. The weight of the sample container 8 per se is determined by subtracting the measurement value by the weight sensor 6 when no sample container 8 is placed, from the measurement value by the weight sensor 6 when the sample container 8 having no sample is placed. And then, the memory 28 stores the value therein.

Subsequently, the sample container 8 having a sample is placed in the sample container placing portion 4. The memory 28 stores therein a measurement value by the weight sensor 6 at this time. The weight of the sample contained in the sample container 8 is determined by subtracting the weight of the sample container 8 per se from the resultant measurement value. And then, the memory 28 stores the value therein. The memory 28 stores therein an upper limit of the amount of sample suctioned from the sample container 8 based on the determined weight of the sample. The upper limit of the sample suction amount set herein may refer to the weight or may be a volume that can be determined by dividing the weight by a specific gravity.

The analyzer sets the analysis contents such as a sample container 8 to be placed in each of the sample container placing portions 4 and the amount of sample to be suctioned from each of the sample containers 8 in the state in which the sample container 8 is placed in a predetermined sample container placing portion 4. At this time, it is confirmed whether or not the measurement value by each of the weight sensors 6 (stored in the memory 28) is equal to the predetermined value set by the analyzer. If the measurement value is not equal to the predetermined value, an alarm is issued for the analyzer to confirm the confirmation whether or not the sample container 8 is placed. In contrast, if the measurement value is equal to the predetermined value, the preparation comes to an end.

[Analysis]

Subsequently, a description will be given below of an analysis with reference to FIGS. 1, 3, and 4.

First of all, the weight of the sample contained in the sample container 8 that contains therein the sample to be suctioned is confirmed by the weight sensor 6. No problem arises in the case of the first sample suction with respect to the sample container 8. However, only the amount of sample smaller than the suction amount may remain in the sample container 8 from the second sample suction onward. In such a case, the sample suction amount setting part 23 sets a new suction amount within the limit of the amount of sample remaining in the sample container 8. The needle 12 is moved to the sample container 8, and then, the tip of the needle 12 is inserted into the sample container 8, thus suctioning the sample by the set amount.

The memory 28 stores therein the measurement value by the weight sensor 6 after the sample is suctioned. An actual sample suction amount is calculated based on a change in measurement value by the weight sensor 6 before and after the sample suction. The actual sample suction amount is compared with the amount previously set by the analyzer, and then, it is confirmed whether or not deficient suction occurs. In the case where the actual sample suction amount is short with respect to the set value by a predetermined amount or more, for example, 10% or more, the short amount is set in the additional suction amount setting part 50 as the additional suction amount, and then, the sample is further suctioned by the amount set in the additional suction amount setting part 50. When the actual sample suction amount is approximate to the set amount, the sample suction amount setting part 23 moves the needle 12 to an injection port in the analyzing device, and then, the sample is injected into the analyzing device. Thereafter, an injection report including information such as the set value of the amount of sample suctioned from each of the sample containers 8, the amount of sample before the suction, the actual sample suction amount, and the existence of the sample container 8 in the sample container placing portion 4 is listed on the display 32, as shown in, for example, Table 1.

TABLE 1

| Sample Container Number | Set Value of Sample Suction Amount (ML) | Sample Amount Before Suction (ML) | Actual Sample Suction Amount (ML) | Remarks |
| --- | --- | --- | --- | --- |
| 1 | 1,000 | 1,500 (1,600 mg) | 900 (990 mg) | |
| 2 | 2,000 | 1,500 (1,700 mg) | 1,450 (1,400 mg) | |
| 3 | 1,500 | 0 (0 mg) | 0 (0 mg) | No Sample Container |

Figure 5:
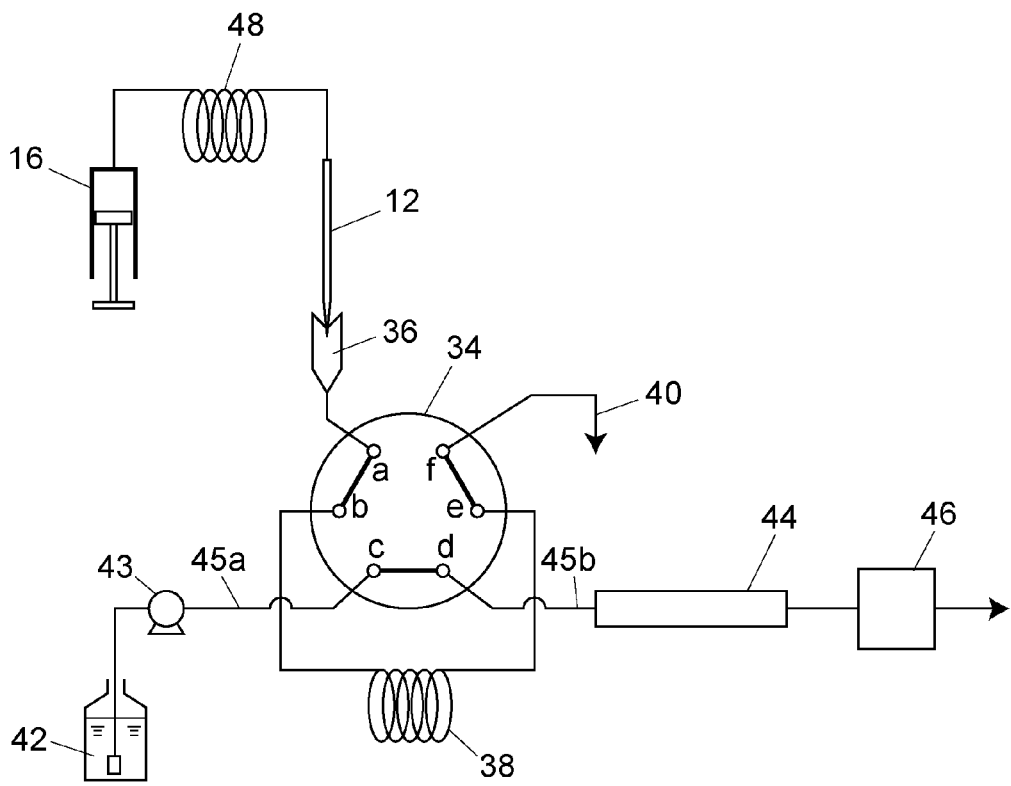
FIG. 5 is a passage diagram illustrating one example of a passage configuration in the automatic sample in the preferred embodiment together with a liquid chromatograph.

Next, an example in which the above-described automatic sampler is applied to a liquid chromatograph will be described with reference to FIG. 5 together with FIG. 1.

The automatic sampler to be applied in this example is called the loop injection system. The amount of sample to be injected to the liquid chromatograph by the metering pump 16 is suctioned from the sample container through the needle 12, to be reserved in a sample loop 48. Thereafter, the needle 12 is moved to an injection port 36, thereby injecting the sample reserved in the sample loop 48 into the injection port 36.

The injection port 36 is connected to a port "a" of a hexagonal valve 34. The hexagonal valve 34 is provided with six ports "a" to "f", and can switch the connection between the adjacent ports. To the ports "b" and "e" are connected both ends of a sample loop 38 for allowing the sample to stay therein. To the port "c" is connected an upstream passage 45a whereas to the port "d" is connected a downward passage 45b. To the port "f" is connected a drain 40. The sample loop 38 has a capacity greater than that of the sample loop 48.

The upstream passage 45a connected to the port "c" is adapted to feed a mobile phase 42 via a liquid feed pump 43. On the downward passage 45b connected to the port "d" are disposed an analysis column 44 and a detector 46. The upstream passage 45a and the downward passage 45b constitute an analysis passage for the liquid chromatograph.

The hexagonal valve 34 can be switched from a state in which the ports "a", "c", and "e" are connected to the ports "b", "d", and "f", respectively, to another state in which the ports "a", "b", and "d" are connected to the ports "f", "c", and "e", respectively, and vice versa. When the sample is injected into the injection port 36 from the needle 12, the hexagonal valve 34 is switched to the state in which the ports "a", "c", and "e" are connected to the ports "b", "d", and "f", respectively, and thereafter, the sample injected from the injection port 36 is reserved in the sample loop 38. After the sample is injected to the injection port 36, the hexagonal valve 34 is switched to the state in which the ports "a", "b", and "d" are connected to the ports "f", "c", and "e", respectively, thereby connecting the upstream passage 45a, the sample loop 38, and the downward passage 45b. In this state, the liquid feed pump 43 feeds the mobile phase 42, so that the sample reserved in the sample loop 38 is transported to the analysis column 44 via the mobile phase 42. Furthermore, each of components of the sample is analyzed, and then, is led to the detector, at which the component is detected.

Although the description has been given of the automatic sampler of the loop injection system in the above-described preferred embodiment, the present invention may be applicable to an automatic sampler of the total amount injection system. Also with the total amount injection system, the amount of sample to be suctioned from the sample container is previously determined, the amount of sample actually suctioned from the sample container is calculated based on a change in measurement value by the weight sensor, and then, the resultant value is compared with the predetermined amount. Thus, it is possible to confirm whether or not deficient suction by the metering pump or the like occurs.

What is claimed is:

1. An automatic sampler comprising:
a sample container placing portion for placing a sample container containing a sample therein;
a sample suction mechanism for suctioning the sample from the sample container placed in the sample container placing portion;
a weight sensor fixed to the sample container placing portion, for measuring a weight of the sample container placed in the sample container placing portion;
a sample suction amount setting part for setting an amount of sample to be suctioned from the sample container by the sample suction mechanism;
a controller for controlling the sample suction mechanism in such a manner that the sample suction mechanism suctions the sample from the sample container by the amount set in the sample suction amount setting part;
a sample amount calculating part for determining an amount of sample in the sample container placed in the sample container placing portion based on a measurement value detected by the weight sensor; and
a sample suction amount calculating part for determining an amount of sample actually suctioned from the sample container based on a change in the amount of sample contained in the sample container, determined by the sample amount calculating part before and after a sample suction by the sample suction mechanism,
wherein the sample suction amount setting part includes an additional suction amount setting part for an amount equal to a shortage as an additional suction amount in the case where the sample suction amount determined by the sample suction amount calculating part is short by a predetermined amount or more with respect to the amount set in the sample suction amount setting part, and
wherein the controller is configured to control the sample suction mechanism in such a manner that the sample suction mechanism further suctions the sample from the sample container by the additional suction amount set in the additional suction amount setting part,
and the automatic sampler further comprising a display configured to display an injection report including at least the amount of sample to be suctioned set in the sample suction amount setting part and an actual sample suction amount including the additional suction amount.

2. The automatic sampler according to claim 1,
wherein the sample suction amount setting part includes a suction amount change setting part for setting again an amount less than or equal to the amount of sample contained in the sample container as a suction amount change when the amount of sample contained in the sample container determined by the sample amount calculating part before a sample suction by the sample suction mechanism is less than the predetermined suction amount.

3. The automatic sampler according to claim 1, further comprising:
a container weight holding part for holding a weight of a sample container in the state in which no sample is contained; and
a sample container recognizing part for issuing an alarm on the display in the case where a measurement value by the weight sensor is less than the weight of the sample container held by the container weight holding part.

* * * * *